United States Patent [19]

Sato et al.

[11] Patent Number: 4,543,207

[45] Date of Patent: Sep. 24, 1985

[54] ELECTRICAL INSULATING OIL AND OIL-FILLED ELECTRICAL APPLIANCES

[75] Inventors: Atsushi Sato, Tokyo; Keiji Endo, Yokohama; Shigenobu Kawakami, Ichikawa; Hitoshi Yanagishita; Shozo Hayashi, both of Yokohama, all of Japan

[73] Assignee: Nippon Petrochemicals Company, Limited, Tokyo, Japan

[21] Appl. No.: 563,741

[22] Filed: Dec. 20, 1983

[30] Foreign Application Priority Data

Dec. 25, 1982 [JP] Japan .................................. 57-233237
Jul. 12, 1983 [JP] Japan .................................. 58-126559

[51] Int. Cl.$^4$ ............................................. C10M 3/10
[52] U.S. Cl. ..................................... 252/570; 585/400; 585/436; 585/444
[58] Field of Search ................ 252/570; 585/436, 400, 585/444

[56] References Cited

U.S. PATENT DOCUMENTS 2,957,036 10/1960 Markus ................................. 260/668
4,442,027 4/1984 Sato et al. ............................ 252/570

FOREIGN PATENT DOCUMENTS 0855004 11/1960 United Kingdom .
2082626 3/1982 United Kingdom .

Primary Examiner—Paul Lieberman
Assistant Examiner—Hoa Van Le
Attorney, Agent, or Firm—Scully, Scott, Murphy & Presser

[57] ABSTRACT

An improved electrical insulating oil and oil-filled electrical appliances impregnated therewith. The electrical insulating oil is quite suitable for use in oil-filled electrical appliances in which insulating materials or dielectric materials made of plastics are employed. The electrical insulating oil comprises (a) an electrical insulating oil except polyaromatic hydrocarbons and (b) an aromatic monoolefin and/or diolefin having two condensed or noncondensed aromatic nuclei.

11 Claims, No Drawings

ELECTRICAL INSULATING OIL AND OIL-FILLED ELECTRICAL APPLIANCES

BACKGROUND OF THE INVENTION (1) Field of the Invention

This invention relates to an electrical insulating oil and oil-filled electrical appliances impregnated with the same.

More particularly, the invention relates to an improved electrical insulating oil and oil-filled electrical appliances in which the insulating oil comprises a mixture of monoolefin and/or diolefin having two aromatic nuclei and an electrical insulating oil or oils other than polyaromatic hydrocarbons. The electrical insulating oil of the invention is quite suitable for use in oil-filled electrical appliances in which insulating materials or dielectric materials made of plastics such as polyolefins are employed.

(2) Description of the Prior Art

Electrical appliances such as oil-filled capacitors, oil-filled power cables and transformers have recently been made to withstand high electric voltages while being small in size. With this tendency, various kinds of plastic films are used together with conventional insulating paper.

In the conventional art, refined mineral oils, polybutenes, alkylbenzenes, polychlorinated biphenyls and the like are used as electrical insulating oils; however, they have several drawbacks. For example, the use of halogenated aromatics such as polychlorinated biphenyls (PCB) was discontinued because it constitutes a public health hazard. Furthermore, the conventional electrical insulating oils are not satisfactorily compatible with the foregoing plastic materials such as polyolefin films which are recently used in oil-filled electrical appliances.

With the requirements of high-voltage withstanding and size reduction, it is necessary that the electrical insulating oil has a high dielectric breakdown voltage, a low dielectric loss tangent, and good hydrogen gas absorbing capacity.

The hydrogen gas absorbing capacity indicates the stability of the insulating oil against corona discharge (partial discharge) under high electric voltage conditions. The higher the gas-absorbing capacity, the smaller the likelihood of corona discharge, which leads to the advantage of the insulating oil having excellent stability or durability.

Meanwhile, in order to meet the requirement of high-voltage use, plastic films such as polyolefin films, polystyrene films and polyester films are used to replace either partially or completely the conventional insulating paper as insulating materials or dielectric materials for electrical appliances such as oil-filled electric cables and capacitors. In view of their dielectric strength, dielectric loss tangent and dielectric constant, polyolefin films, especially polypropylene and cross-linked polyethylene films, are preferred as the plastic films.

When these polyolefin films are impregnated with insulating oils, some oils cause the films to swell to some extent. If a film becomes swollen, the thickness of the insulating layer increases. As a result, the resistance to the flow of insulating oil increases in electrical cables, and insufficient impregnation with insulating oil occurs in electric capacitors, causing the formation of voids (unimpregnated portions) and the undesirable lowering of the corona discharge voltage.

BRIEF SUMMARY OF THE INVENTION

In view of the above-described conventional state of the art, it is the primary object of the present invention to provide an improved electrical insulating oil and oil-filled electrical appliances which are impregnated with the electrical insulating oil and are free from the above-described disadvantages in the conventional art.

Another object of the present invention is to provide an electrical insulating oil which has an excellent dielectric constant and other electrical properties, which has a good hydrogen gas absorbing capacity, and which is highly compatible with plastic film insulating materials.

It is a further object of the present invention to provide oil-filled electrical appliances which have excellent corona discharge characteristics, dielectric breakdown voltage and other advantageous electrical characteristics, and have a long service life.

The present invention is, therefore, concerned with a novel and improved electrical insulating oil and electrical appliances which are impregnated with this oil.

The electrical insulating oil of this invention comprises:

(a) at least one electrical insulating oil other than polyaromatic hydrocarbon, and (b) at least one of monoolefins and/or diolefins having two condensed or noncondensed aromatic nuclei.

DETAILED DESCRIPTION OF THE INVENTION

The present invention will be described in more detail.

The electrical insulating oils in item (a) are conventionally known ones other than polyaromatic hydrocarbons. The polyaromatic hydrocarbons herein referred to are those each of which has two or more condensed or noncondensed aromatic nuclei but has no olefinic unsaturation. They are exemplified by diarylalkanes such as phenylxylylethane, diarylcycloalkanes, alkylbiphenyls such as monoisopropylbiphenyl, cycloalkylbiphenyls, alkylnaphthalenes such as diisopropylnaphthalene, cycloalkylnaphthalenes, triarylalkanes, terphenyl, arylnaphthalenes, and aralkylnaphthalenes. Halogenated polyaromatic hydrocarbons such as PCB are also included.

Accordingly, the electrical insulating oils in item (a) are exemplified by monoaromatic hydrocarbons, aliphatic olefin oligomers, organic acid esters, animal or vegetable oils, mineral oils, silicone oils, and aromatic ethers.

More particularly, the above-mentioned monoaromatic hydrocarbons are exemplified by alkylbenzenes such as dodecylbenzene, cycloalkylbenzenes such as cyclohexylbenzene, partially hydrogenated condensed aromatics such as alkylindanes or tetralin.

The above-mentioned aliphatic olefin oligomers are exemplified by polybutenes or poly-α-olefins.

The aforementioned organic acid esters are more exemplified by aromatic esters such as diethyl phthalate, dibutyl phthalate, dioctyl phthalate including di-(2-ethylhexyl)phthalate, diisodecyl phthalate, nonyl benzoate, trioctyl trimellite, and triisodecyl trimellite; cycloaliphatic acid esters such as di-(2-ethylhexyl) tetrahydrophthalate and diisodecyl tetrahydrophthalate; aliphatic acid esters such as dioctyl adipate, diisodecyl adipate, dibutyl adipate, and dioctyl sebacate.

The aforementioned animal or vegetable oils are exemplified by castor oil, soybean oil, and cotton seed oil.

Although the foregoing aromatic ethers are exemplified by alkyl-aryl ethers such as anisole, the aromatic ethers having two condensed or noncondensed aromatic nuclei are preferable because of their appreciable synergistic effect. Those aromatic ethers are exemplified by diaryl ethers such as phenyl tolyl ether, ditolyl ether, phenyl xylyl ether, phenyl cumenyl ether, and phenyl sec-butyl ether; aryl aralkyl ethers such as ethylphenyl benzyl ether, propylphenyl benzyl ether, cumenylphenyl benzyl ether, and phenyl phenylpropyl ether; diaralkyl ethers such as dibenzyl ether, diphenethyl ether, bis(α-methylbenzyl) ether, and benzyl phenethyl ether; alkoxy or cycloalkoxy diaryl alkanes such as methoxydiphenyl methane, ethoxydiphenyl methane, and propoxydiphenyl ethane; alkoxy or cycloalkoxy diaryls such as methoxy biphenyl, ethoxy biphenyl, propoxy biphenyl, and isopropoxy biphenyl; alkoxy or cycloalkoxy naphthalenes such as methoxynaphthalene, methoxymethylnaphthalene, ethoxynaphthalene, propoxynaphthalene, isopropoxynaphthalene, butoxynaphthalene, sec-butoxynaphthalene, and isobutoxynaphthalene.

As the electrical insulating oils except polyaromatic hydrocarbons of item (a), the above oils can be used singly or in a mixture of two or more kinds and the viscosity of the oil is preferably not higher than $3 \times 10^{-5}$ m$^2$/s (30 cSt) at 40° C., and more preferably not higher than $10^{-5}$ m$^2$/s (10 cSt) at 40° C.

The compounds that are used together with the foregoing electrical insulating oils of item (a) are aromatic monoolefins and/or diolefins each having two aromatic nuclei of item (b). As these aromatic olefins, they are derivatives of aliphatic olefins and derivatives of alicyclic olefins such as cyclopentene and cyclohexene, which are exemplified by the following compounds represented by general formulae (I) to (VII). The general formulae (I) to (IV) represent monoolefins and formulae (V) to (VII) represent diolefins.

General formula:

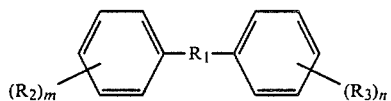
(I)

wherein $R_1$ is an alkenylene group or a cycloalkenylene group having an unsaturated double bond, each of m and n is an integer from zero to 3, inclusive, and $R_2$ of m in number and $R_3$ of n in number are respectively the same or different from one another and each of them is a hydrogen atom or an alkyl group.

General formula:

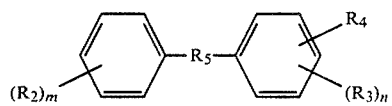
(II)

wherein $R_4$ is an alkenyl group or a cycloalkenyl group, $R_5$ is an alkylene group or a cycloalkylene group having no olefinic unsaturation, each of m and n is an integer from zero to 3, inclusive, and $R_2$ of m in number and $R_3$ of n in number are respectively the same or different from one another and each of them is a hydrogen atom or an alkyl group.

General formula:

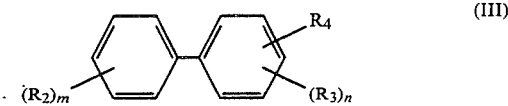
(III)

wherein $R_4$ is an alkenyl group or a cycloalkenyl group, each of m and n is an integer from zero to 3, inclusive, and $R_2$ of m in number and $R_3$ of n in number are respectively the same or different from one another and each of them is a hydrogen atom or an alkyl group.

General Formula:

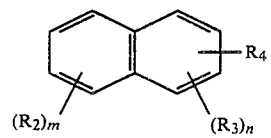

wherein $R_4$ is an alkenyl group or a cycloalkenyl group, each of m and n is an integer from zero to 3, inclusive, and $R_2$ of m in number and $R_3$ of n in number are respectively the same or different from one another and each of them is a hydrogen atom or an alkyl group.

General Formulae:

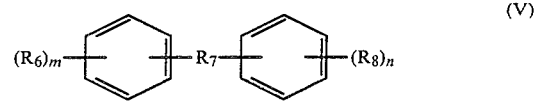
(V)

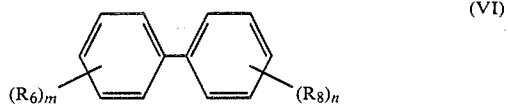
(VI)

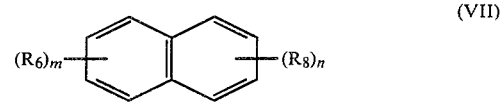
(VII)

wherein $R_6$, $R_7$ and $R_8$ are hydrocarbon residual groups, respectively, each of m and n is an integer from zero to three, inclusive, $R_6$ of m in number, $R_7$, and $R_8$ of n in number are either the same or different substituent groups, and the total number of double bonds in the substituent groups is two in each formula.

In the foregoing general formula (I), the alkenylene group or cycloalkenylene group of $R_1$ is a substituent group which is made by removing two hydrogen atoms from a compound such as ethylene, propylene, butene, isobutene, pentene, methylpentene, hexene, cyclopentene, cyclohexene, or alkylcyclohexene. The alkyl groups of $R_2$ and $R_3$ are exemplified by methyl, ethyl, propyl, isopropyl, n-butyl, isobutyl, sec-butyl, tert-butyl and amyl groups.

The compounds represented by formula (I) are exemplified by stilbene, 4-methylstylbene, 1,2-diphenylpropene, 1,3-diphenylpropene, 1,4-diphenylbutene-1, 1,4-diphenylbutene-2, 1,1-diphenylethylene, 1-phenyl-1-(4-ethylphenyl)ethylene, 1,1-diphenylpropene-1, 2,3-diphenylpropene, 1,2-diphenylbutene-2, 1,3-diphenylbutene-1, 2,4-diphenyl-4-methylpentene-1, 1,2-diphenylcyclohexene, and phenylbenzylcyclohexene.

These compounds can be prepared by dimerization or codimerization of styrenes such as styrene, α-methylstyrene and vinyltoluene in the presence of an acid catalyst.

Further, 1,2-diphenylethylene is prepared by reacting benzaldehyde with benzylmagnesium bromide and then dehydrating the reaction product. 1,2-diphenylpropene is prepared in a similar manner. Furthermore, 1,1-diphenylethylene is prepared by reacting diphenylketone with a Grignard reagent such as methylmagnesium iodide which is followed by dehydration.

The symbol $R_4$ in formula (II) is an alkenyl group or a cycloalkenyl group such as vinyl, propenyl, isopropenyl, allyl, butenyl, cyclopentenyl or cyclohexenyl group. $R_5$ is a divalent substituent group which is made by removing two hydrogen atoms from a saturated aliphatic hydrocarbon or a saturated alicyclic hydrocarbon such as cyclopentane, cyclohexane or cycloheptane. $R_2$ and $R_3$ of alkyl groups are the same as those in formula (I).

The compounds represented by formula (II) are exemplified by 1-phenyl-1-(4-vinylphenyl)ethane, 1-(4-methylphenyl)-1-(4-vinylphenyl)ethane, 1-phenyl-1-(4-isopropenylphenyl)ethane, phenyl-(4-vinylphenyl)methane, and phenyl(cyclohexenylphenyl)methane.

These compounds can be prepared through various chemical synthesis methods. For example, phenyl(vinylphenyl)ethane is prepared by reacting diphenylethane with acetyl chloride in the presence of Friedel-Crafts catalyst to obtain phenyl(acetylphenyl)ethane, then it is reduced with sodium borohydride and dehydrated. Phenyl(isopropenylphenyl)ethane is prepared by reacting phenyl(formylpheny)ethane with a Grignard reagent such as methylmagnesium iodide, which is followed by dehydration.

In formula (III), $R_4$ is an alkenyl group or a cycloalkenyl group the same as $R_4$ in formula (II), and $R_2$ and $R_3$ of alkyl groups formula (III) are also the same as those in formula (II).

The compounds represented by formula (III) are exemplified by 2-isopropenylbiphenyl, 4-isopropenylbiphenyl, 2-isopropenyl-4'-isopropylbiphenyl, cyclohexenylbiphenyl, and cyclopentenylbiphenyl. Among these compounds, for example, isopropenylbiphenyl prepared by dehydrogenation of isopropylbiphenyl.

In formula (IV), $R_4$ is an alkenyl group or a cycloalkenyl group is the same as those of formula (II) and $R_2$ and $R_3$ of formula (IV) are the same as those of formula (II).

The compounds represented by formula (IV) are exemplified by α-vinylnaphthalene, isopropenylnaphthalene, allylnaphthalene, and 1-cyclopent-2-enylnaphthalene. Among them, for example, vinylnaphthalene is prepared by reacting formylnaphthalene with a Grignard reagent such as methylmagnesium iodide, which is followed by dehydration.

In the foregoing general formulae (V) to (VII), in the case where $R_6$ or $R_8$ is an unsaturated group, it is an alkenyl or cycloalkenyl group, and is exemplified by vinyl, propenyl, isopropenyl, allyl, butenyl, and cyclohexenyl group.

In the case where $R_6$ or $R_8$ is a saturated group, it is an alkyl or cycloalkyl group, and is exemplified by a methyl, ethyl, n-propyl, isopropyl, n-butyl, isobutyl, sec-butyl, tert-butyl, pentyl and cyclohexyl group.

In the case where $R_7$ is an unsaturated group, it is an alkenylene or cycloalkenylene group, and is exemplified by a divalent substituent group which is obtained by removing two hydrogen atoms from an olefinic hydrocarbon such as ethylene, propylene, butene, cyclopentene, and cyclohexene.

Furthermore, in the case where $R_7$ is a saturated group, it is an alkylene or cycloalkylene group, and is exemplified by divalent substituent groups which are obtained by removing two hydrogen atoms from a saturated hydrocarbon such as methane, ethane, propane, butanes and cyclohexane.

The following compounds are exemplified as those represented by the foregoing formulae (V), (VI) and (VII).

Compounds represented by formula (V):
1-phenyl-1-(4'-vinylphenyl)ethylene;
1,1-diphenylbutadiene;
2,4-diphenyl-1,3-pentadiene;
bis(4-isopropenylphenyl)methane;
1,1-bis(4-isopropenylphenyl)ethane;
1,2-bis(4-isopropenylphenyl)ethane; and
1,1-bis(vinylphenyl)ethane.

Compounds represented by formula (VI):
2,2'-divinylbiphenyl and 4,4'-diisopropenylbiphenyl.

Compounds represented by formula (VII):
divinylnaphthalene and diisopropenylnaphthalene.

The above compounds are shown as examples of the components which can be used in the preparation of the insulating oil composition of this invention, and the materials which may be used for the present invention are by no means restricted to the above exemplary compounds.

Still further, the aromatic monoolefin and/or diolefin used in this invention are prepared by employing reactions of dehydrogenation, oxidative dehydrodimerization and decomposition.

More particularly, in a method employing dehydrogenation, a saturated aromatic hydrocarbon corresponding to the aromatic monoolefin of the invention, or a saturated aromatic hydrocarbon or an aromatic monoolefin corresponding to the aromatic diolefin of the invention is dehydrogenated in the presence of a suitable dehydrogenation catalyst with suppressing side reactions of decomposition and polymerization.

In the reaction, the dehydrogenation catalyst is not restricted to any specific one. For example, the dehydrogenation catalysts are exemplified by one or a mixture of oxides of metals such as Cr, Fe, Cu, K, Mg and Ca or precious metals such as Pt and Pd, or these metal oxides or precious metals which are supported on a carrier such as alumina.

The reaction temperature of the dehydrogenation is in the range of 350° to 650° C., preferably 400° to 600° C. The LHSV (liquid hourly space velocity) of the dehydrogenation is in the range of 0.2 to 10, preferably 0.5 to 3.0. In the dehydrogenation; steam, nitrogen gas or hydrogen gas can be introduced into the reaction system in order to reduce partial pressures and to avoid the formation of carbon. Further, if necessary, a suitable diluent can be used. When the rate of dehydrogenation is not so high, raw materials themselves conveniently serve as a diluent.

Through the above procedures, for example, diphenylethylene is obtained from diphenylethane; vinylphenyl-phenylethane, from ethylphenyl-phenylethane; and vinylphenyl-phenylethylene, from ethylphenyl-phenylethylene. Further, isopropenyl biphenyl is obtained from isopropyl biphenyl; and isopropenyl-isopropylnaphthanene or diisopropenylnaphthalene, from diisopropylnaphthalene.

The aromatic monoolefins used in the present invention can also be prepared by oxidative dehydrodimerization method. In this method, methyl-substituted monocyclic aromatic hydrocarbon such as toluene, xylene, ethyltoluene and vinyltoluene are subjected to dimerization (coupling) together with dehydrogenation.

For example, 1,2-diphenylethylene is obtained from toluene, and 1,2-di(methylphenyl)ethylene, from xylene. In this reaction, a saturated aromatic hydrocarbon corresponding the obtained olefin, for example, 1,2-diphenylethane from toluene, is simultaneously obtained, which is convenient for preparing the electrical insulating oil of the present invention.

Any suitable catalyst can be used for this oxidative dehydrodimerization. For example, usable catalysts are copper chromite catalysts containing Ni, Ta or Ti as disclosed in Japanese Patent Publication No. 49-6312 (1974), the catalysts of oxides of metals such as Bi, Pb, Te, Ba, Tl and Cd or their mixture as disclosed in Japanese Patent Publication No. 49-20561 (1974), and composite oxide catalyst of Tl as disclosed in U.S. Pat. No. 4,243,825. Further, alkali metal oxides as promoters can be added to these catalysts.

This reaction can be carried out in the presence of molecular oxygen with the above-described catalyst. The molar ratio of oxygen/methyl-substituted aromatic hydrocarbon is in the range of 0.01 to 5.0, preferably 0.05 to 1.0. Meanwhile, the reaction can be performed stoichiometrically without the presence of molecular oxygen, in which oxidation treatment in addition to usual treatment to remove deposited carbon, is necessary because the oxide catalyst is reduced with the progress of reaction.

The reaction temperature is in the range of 300° to 800° C., and preferably 500° to 700° C. The contact time is in the range of 0.01 second to several minutes, and preferably 0.1 to 30 seconds. The pressure in this reaction is not restricted and can range from a reduced pressure to 100 atmospheric pressure (98 bar), but preferably in the range of 0.1 to 5.0 atmospheric pressure (0.098 to 4.9 bar).

Further, the aromatic olefins used in the present invention can also be prepared by decomposition such as thermal cracking and catalytic cracking, in which, for example, triarylalkanes, diaralkyl aromatic hydrocarbons and polymers of styrenes are employed as raw materials.

In the thermal cracking of the above raw materials, the reaction temperature is set in the range of 300° to 700° C., and preferably in the range of 330° to 600° C. When the reaction temperature is too low, the rate of decomposition becomes very low. On the other hand, when the reaction temperature is too high, the raw material is decomposed to monocyclic hydrocarbons. Accordingly, in order to obtain the aromatic hydrocarbons used in the present invention at a higher yield, it is advisable that the thermal cracking is performed at a relatively higher temperature with a shorter retention time.

In the catalytic cracking, silica, silica gel, silica-alumina, kaolin, zeolite (with or without de-aluminum treatment), and organic or inorganic sulfonic acid can be used. The reaction is performed in a liquid phase or gas phase, and the reaction temperature is in the range of 300° to 700° C., and preferably in the range of 330° to 600° C.

The above-mentioned monoolefin and/or diolefin having two condensed or noncondensed aromatic nuclei is/are employed as a mixture with the electrical insulating oil of item (a). Accordingly, provided the monoolefin and/or diolefin can be mixed and dissolved into the insulating oil of (a) and produce a liquid mixture at ordinary temperatures, the olefins themselves can be either liquid or solid. The above olefin having two aromatic nuclei can be used singly or in a mixture of two or more kinds.

In the present application, as described above, the electrical insulating oil is prepared by mixing the electrical insulating oil except polyaromatic hydrocarbon of item (a) and the aromatic olefin of item (b). The viscosity of the thus prepared insulating oil of the invention is preferably not higher than 30 cSt ($3 \times 10^{-5}$ m$^2$/s) and more preferably not higher than 10 cSt ($10^{-5}$ m$^2$/s) at 40° C. Accordingly, in order to obtain a mixture having a viscosity of the above value, components are suitably selected from the foregoing electrical insulating oils of item (a) and from the foregoing compounds of formulae (I) to (VII) as aromatic olefins of (b).

According to the present invention, in spite of the mixing with the unsaturated compounds of the aromatic olefins, no deterioration in biodegradability, thermal stability and oxidation stability is observed in practical uses, while various electrical properties can be improved.

The mixing ratio of the electrical insulating oil of (a) and the aromatic olefin of (b) is arbitrary. However, a ratio of 0.01 to 50 wt % of the aromatic olefin with respect to the mixture of both component materials is preferable in view of their synergistic effects. The more preferable quantity of the aromatic olefin is 1.0 to 30% by weight.

In order to improve further the oxidation stability, several known antioxidants can be added to the electrical insulating oil of the present invention. As such antioxidants, there are phenol compounds such as 2,6-di-tert-butyl-p-cresol, 2,2'-methylenebis(4-methyl-6-tert-butylphenol), 4,4'-butylidenebis(3-methyl-6-tert-butylphenol), 4,4'-thiobis(3-methyl-6-tert-butylphenol), stearyl-β-(3,5-di-tert-butyl-4-hydroxyphenol)propionate, tetrakis[methylene-3(3',5'-di-tert-butyl-4'-hydroxyphenyl)-propionate]methane, 1,3,5-trimethyl-2,4,6-tris(3,5-di-tert-butyl-4-hydroxybenzyl)benzene, and 1,1,3-tris(2-methyl-4-hydroxy-5-tert-butylphenol)butane; sulfur compounds such as dilauryl thiodipropionate, distearyl thiodipropionate, laurylstearyl thiodipropionate, and dimyristyl thiodipropionate; and phosphorous compounds such as triisodecylphosphite, diphenylisodecylphosphite, triphenylphosphite, and trinonylphenylphosphite.

These antioxidants can be added to the electrical insulating oil singly or in combination of two kinds or more. The addition quantity of the antioxidant is 0.001 to 5% by weight and preferably 0.01 to 2.0% by weight of the electrical insulating oil.

Furthermore, in order to impart a nonflammable property and other desirable effects to the electrical insulating oil of the present invention, several known additives such as phosphoric esters and epoxy compounds can be added to the electrical insulating oil.

The electrical insulating oil of the present invention is good for general uses and, in particular, it is advantageous for the impregnation of oil-filled electrical appliances such as electric capacitors, power cables and transformers.

As described at the beginning of this specification, the requirements of high-voltage withstanding and size reduction of such oil-filled electrical appliances have become severe in recent years. In order to meet these requirements, plastics are used to replace either partially or totally the conventional insulating paper as insulating materials or dielectric materials for the oil-filled electrical appliances. More particularly, as electrical insulating materials (dielectric materials) of electric capacitors, there is proposed the use of a combination of insulating paper and plastic films such as stretched or nonstretched polypropylene, polymethylpentene, or polyester film; the use of these plastic films singly; the use of embossed films of these plastic films to facilitate impregnation with the insulating oil; or the use of metallized plastic films, wherein the metallic layer serves as an electrode. In the case of oil-filled cables, the electrical insulating materials are made of polyolefin film such as cross-linked or non-cross-linked polyethylene film, stretched or nonstretched polypropylene film, and polymethylpentene film; paper-polyolefin laminated film made by the extrusion of polyolefin onto paper; composite film which is made by cross-linking insulating paper with silane-grafted polyethylene in the presence of a silanol condensation catalyst; or an artificial paper sheet which is made by mixing wood pulp and polyolefin fiber.

The electrical insulating oil of the present invention is excellent in compatibility with plastic materials. Accordingly, the electrical insulating oil is quite suitable for use in oil-filled electrical appliances such as electric capacitors and electric cables in which plastic materials are used for either part or all of the insulating material or dielectric material.

More particularly, when an electric capacitor is provided with an insulating (dielectric) material that is partially or totally made of plastics, especially polyolefin, and when it is impregnated with the electrical insulating oil of the present invention, the insulating material can be fully and completely impregnated with the electrical insulating oil because swelling of the insulating material is slight, and voids (unimpregnated portions) are not formed. Accordingly, corona discharge due to the convergence of electric fields to the voids hardly occurs, and dielectric breakdown can be well avoided. Furthermore, the electrical insulating oil of the present invention has excellent hydrogen gas absorbing capacity and corona discharge resistance under high-voltage stress, so that it is possible to obtain both a long service life and high-voltage use of the electrical appliances.

In the case of electric power cables, a change in dimensions of the insulating material due to swelling is small, and resistance to the insulating oil flow can be made low so that oil impregnation can be performed in a short time. Of course, it will be understood that, because of the ease of impregnation, voids are hardly formed and the dielectric breakdown voltage becomes higher. When a cable is made by using an insulating material of a laminated film or composite film made of plastic material and paper, peeling, creasing and buckling of the insulating material upon bending of the cable does not occur even when the insulating material has been in contact with the electrical insulating oil for a long time. Further, as in the case of the electric capacitor, a power cable having a good corona discharge resistance can be obtained due to the excellent hydrogen gas absorbing capacity of the electrical insulating oil. Accordingly, it is also possible to obtain a long service life and high-voltage use, as for the capacitors.

According to the present invention, the above-described advantageous features can be improved by impregnation with the electrical insulating oil consisting of a plurality of specific component materials, owing to the synergistic effect between the component materials. Further, the good electrical characteristics, biodegradability, thermal resistance, and oxidation stability of each component material can be well maintained, and at the same time, the viscosity and pour point of the electrical insulating oil composition can be adjusted within desired ranges. Therefore, the manufacture of oil-filled electrical appliances is facilitated, and oil-filled electrical appliances exhibiting high performance under any use conditions can be obtained.

In the following, the electrical insulating oil and electrical appliances impregnated therewith according to the present invention will be described in more detail with reference to several examples.

EXAMPLES

The monoolefins and/or diolefins having two condensed or noncondensed aromatic nuclei used in the invention can be prepared by various known methods as described above. For reference purpose, however, the preparation of two compounds of item (b) employed in the following examples will be described because they are hardly available in commercial production.

PREPARATION EXAMPLE 1

Preparation of 1-phenyl-1-(4'-vinylphenyl)ethane

Synthesis of Ketone

To a 5 liter reaction vessel equipped with a stirrer, reflux condenser and dropping funnel were added 2 liters of carbon tetrachloride and 475 g of anhydrous aluminum chloride, and the contents were cooled by ice while being stirred. This was followed by the addition of 275 g of acetyl chloride through the dropping funnel and additional stirring for 1 hour. To this was added 546 g of 1,1-diphenylethane, and the contents were stirred for 4 hours. After the reaction, the aluminum chloride was deactivated by diluted hydrochloric acid and the reaction mixture was rinsed with an aqueous solution of sodium carbonate. The reaction medium was then removed by distillation to obtain 502 g of ketone in a yield of 74.7%.

Synthesis of Alcohol

To a 2 liter reaction vessel equipped with a stirrer, reflux condenser and dropping funnel were added 600 ml of isopropyl alcohol and 84 g of sodium borohydride, and the isopropyl alcohol was refluxed by heating the vessel. The ketone (500 g) was added dropwise for 1 hour to this mixture and the reaction mixture was stirred further with refluxing of the isopropyl alcohol.

After the reaction, the catalyst was deactivated by adding water. The reaction product was separated by ether extraction and was dried by anhydrous sodium sulfate. The ether was distilled off to obtain 480 g of alcohol in a yield of 95.2%.

Synthesis of 1-phenyl-1-(4'-vinylphenyl)ethane

A 500 ml three neck flask was equipped with a dropping funnel, 40 g of potassium hydrogensulfate was fed into the flask, and it was heated to 230° to 240° C. under a reduced pressure. The above-obtained alcohol (480 g) was then added through the dropping funnel. The alcohol was dehydrated to produce an olefin, which olefin was immediately collected by distillation into an outer receptacle. By removing water from the obtained olefin, 332 g of 1-phenyl-1-(4'-vinylphenyl)ethane was obtained in a yield of 75.2% (b.p. 149° C./10 mmHg, 113° C./2 mmHg).

The chemical structure of the final product was identified by elemental analysis, IR spectrum analysis and NMR spectrum analysis.

PREPARATION EXAMPLE 2

Preparation of 1-phenyl-1-(4'-vinylphenyl)ethylene

A Grignard reagent was prepared by adding 14.6 g (0.601 mole) of magnesium to 250 ml of dried tetrahydrofuran, heating the mixture to 65° C., and adding dropwise 100 g (0.546 mole) of p-bromostyrene. This reagent was then cooled to 20° C. and 65.5 g (0.546 mole) of acetophenone was added dropwise to the reagent. The reaction mixture was placed in a mixture of 500 g of crushed ice, 500 g of water and 15 ml of 98% sulfuric acid.

After that, a reaction product of alcohol was obtained by ether extraction. This alcohol was then dehydrated by potassium hydrogensulfate to obtain 62.8 g of 1-phenyl-1-(4'-vinylphenyl)ethylene in a yield of 56%, which compound was liquid at ordinary temperatures (b.p. 151° C./10 mmHg, 114° C./2 mmHg).

The chemical structure of the final product was identified by elemental analysis, IR spectrum analysis and NMR spectrum analysis.

EXAMPLES OF ELECTRICAL INSULATING OILS

As indicated in the following Tables 1 to 3, electrical insulating oils except polyaromatic hydrocarbon of item (a) were mixed with aromatic monoolefins and/or diolefins of item (b) to prepare the electrical insulating oils of the present invention.

In these tables, electrical insulating oil Nos. 1, 6, 10, 13, 16, 19, 27 and 28 are comparative examples and the others are examples of the invention.

In connection with electrical insulating oil Nos. 1 to 15, capacitors were prepared by using single-side metallized paper as electrodes and dielectric materials, which capacitors were impregnated with the electrical insulating oils. The capacitances of the capacitors which were impregnated with electrical insulating oil Nos. 1 to 9 were 2.5 μF and those impregnated with oil Nos. 10 to 15 were 2.8 μF.

The capacitors which were impregnated with electrical insulating oil Nos. 1 to 15 were applied with an electric voltage of 500 V for 100 hours and capacitances and dielectric loss tangents before and after the voltage application were measured. From these results, ratios of decrease in capacitances and ratios of increase in dielectric loss tangents were calculated, which are shown also in Table 1.

According to the results shown in Table 1, it will be understood that the electrical insulating oils containing the foregoing aromatic monoolefins and/or diolefins gave small ratios of changes in capacitances and dielectric loss tangents and that the performance of the basic oils was much improved.

In connection with electrical insulating oil Nos. 16 to 18 in Table 2, capacitors were made by winding the following materials for electrode and dielectric, and they were impregnated with the electrical insulating oils. The capacitances of them were 0.68 μF.

Electrode: Aluminum foil of 7μ in thickness and 50 mm in width.

Dielectric: Two-ply film of paper of 12μ thickness, 62 mm width and polypropylene film of 28μ thickness, 62 mm width.

With regard to these capacitors, corona starting voltages (CSV) and corona ending voltages (CEV) were measured, the results of which are shown in Table 2.

From the results shown in Table 2, it will be understood that electrical insulating oil Nos. 17 and 18 of the invention containing the aromatic olefin gave higher values of CSV and CEV, and that the performance of the electrical insulting oils was much improved.

In connection with electrical insulating oil Nos. 19 to 32 in Table 3, which contain ethereal oils, capacitors were made by winding two-ply capacitor-use polypropylene film (each 14μ thickness) as a dielectric material and aluminum foil as electrodes. They were then impregnated with the electrical insulating oils. The capacitance of them was 0.45 μF.

With regard to these capacitors, corona starting voltages (CSV) and corona ending voltages (CEV) were measured, the results of which are shown in Table 3.

Breakdown times under a fixed voltage were also measured and the results of this test are also shown in Table 3. In the test for breakdown times, each value was calculated such that seven capacitors impregnated with the same oil were tested and the maximum value and minimum value were neglected and the average of the other five breakdown times was adopted as the resultant value. Furthermore, the breakdown times were represented by the values relative to the values of base oils having substantially no olefinic unsaturation.

From the results shown in Table 3, it will be understood that the electrical insulating oils of the invention containing the aromatic olefins also exhibited better results and that the performance of the electrical insulating oils was much improved. Incidentally, the electrical insulating oil No. 27 containing hexadecene-1 was not good.

TABLE 1

| Insulating Oil No. | Electrical Insulating Oil | | | | Kinematic Viscosity (cSt at 30° C.) | Ratio of Decrease in Capacitance (%) | Ratio of Increase in Dielectric Loss Tangent (%) |
| --- | --- | --- | --- | --- | --- | --- | --- |
| | Insulating Oil of (a) | wt % | Aromatic Olefin of (b) | wt % | | | |
| 1 | Mineral oil | 100 | — | — | 11.6 | 2.3 | 30.0 |
| 2 | " | 90 | 1,3-diphenyl-butene-1 | 10 | 10.9 | 0.3 | 18.5 |
| 3 | " | 90 | 2,4-diphenyl-4-methylpentene-1 | 10 | 11.3 | 0.2 | 15.5 |
| 4 | " | 90 | 1,1-diphenyl-ethylene | 10 | 10.4 | 0.1 | 13.3 |

TABLE 1-continued

| Insulating Oil No. | Electrical Insulating Oil | | | | Kinematic Viscosity (cSt at 30° C.) | Ratio of Decrease in Capacitance (%) | Ratio of Increase in Dielectric Loss Tangent (%) |
|---|---|---|---|---|---|---|---|
| | Insulating Oil of (a) | wt % | Aromatic Olefin of (b) | wt % | | | |
| 5 | " | 92 | 1-phenyl-1-(4'-vinylphenyl)-ethylene | 8 | 10.7 | 0.1 | 12.1 |
| 6 | Polybutene | 100 | — | — | 6000 | 6.8 | 29.5 |
| 7 | " | 90 | 2,4-diphenyl-4-methylpentene-1 | 10 | 2060 | 0.7 | 15.8 |
| 8 | " | 90 | 1,1-diphenyl-ethylene | 10 | 1650 | 0.3 | 11.3 |
| 9 | " | 92 | 1-phenyl-1-(4'-vinylphenyl)-ethylene | 8 | 1720 | 0.2 | 11.0 |
| 10 | Dioctylphthalate | 100 | — | — | 43.7 | 1.3 | 30.9 |
| 11 | " | 90 | 1,1-diphenyl-ethylene | 10 | 32.1 | 0.0 | 15.3 |
| 12 | " | 92 | 1-phenyl-1-(4'-vinylphenyl)-ethylene | 8 | 34.6 | 0.0 | 15.6 |
| 13 | Castor oil | 100 | — | — | 250 | 1.6 | 28.7 |
| 14 | " | 90 | 2,4-diphenyl-4-methylpentene-1 | 10 | 155 | 0.3 | 14.6 |
| 15 | " | 92 | 1-phenyl-1-(4'-vinylphenyl)-ethylene | 8 | 163 | 0.2 | 13.9 |

TABLE 2

| Insulating Oil No. | Electrical Insulating Oil | | | | Kinematic Viscosity (cSt at 30° C. | CSU (kV) | CEV (kV) |
|---|---|---|---|---|---|---|---|
| | Insulating Oil of (a) | wt % | Aromatic Olefin of (b) | wt % | | | |
| 16 | Dodecylbenzene | 100 | — | — | 12.5 | 2.8 | 1.8 |
| 17 | " | 90 | 2,4-diphenyl-4-methylpentene-1 | 10 | 11.9 | 3.3 | 2.2 |
| 18 | " | 90 | 1,1-diphenyl-ethylene | 10 | 11.1 | 3.4 | 2.3 |

TABLE 3

| Insulating Oil No. | Electrical Insulating Oil | | | | Kinematic Viscosity (cSt at 30° C.) | CSV (kV) | CEV (kV) | Breakdown Time (Relative Value) |
|---|---|---|---|---|---|---|---|---|
| | Insulating Oil of (a) | wt % | Olefin | wt % | | | | |
| 19 | Ditolyl ether | 100 | — | — | 4.5 | 2.8 | 2.2 | 1.0 |
| 20 | " | 90 | 1-phenyl-1-(4'-vinylphenyl)-ethane | 10 | 4.4 | 3.5 | 2.4 | 6.2 |
| 21 | " | 90 | 1,1-diphenyl-ethylene | 10 | 4.2 | 3.4 | 2.4 | 5.5 |
| 22 | " | 90 | 2,4-diphenyl-4-methylpentene-1 | 10 | 5.1 | 2.9 | 2.3 | 3.5 |
| 23 | " | 92 | 1-phenyl-1-(4'-vinylphenyl)-ethylene | 8 | 4.4 | 3.5 | 2.4 | 6.0 |
| 24 | " | 90 | 1-phenyl-1-(4'-vinylphenyl)-ethane / 1-phenyl-1-(4'-vinylphenyl)-ethylene | 6 / 4 | 4.3 | 3.5 | 2.3 | 5.8 |
| 25 | " | 90 | isopropenyl-biphenyl | 10 | 4.6 | 3.4 | 2.3 | 5.0 |
| 26 | " | 90 | α-vinylnaphthalene | 10 | 4.4 | 3.5 | 2.4 | 6.5 |
| 27 | " | 90 | hexadecene-1 | 10 | 4.1 | 2.9 | 2.3 | 1.2 |
| 28 | Bis(-methylbenzyl) ether | 100 | — | — | 9.6 | 2.7 | 2.1 | 1.0 |
| 29 | Bis(-methylbenzyl) ether | 90 | 1-phenyl-1-(4'-vinylphenyl)-ethane | 10 | 7.9 | 3.3 | 2.4 | 6.6 |
| 30 | Bis(-methylbenzyl) ether | 90 | 1,1-diphenyl-ethylene | 10 | 7.7 | 3.3 | 2.3 | 5.5 |
| 31 | Bis(-methylbenzyl) ether | 90 | 2,4-diphenyl-4-methylpentene-1 | 10 | 8.2 | 2.9 | 2.3 | 4.3 |
| 32 | Bis(-methyl- | 92 | 1-phenyl-1- | 8 | 7.9 | 3.4 | 2.4 | 6.1 |

TABLE 3-continued

| Insulating Oil No. | Electrical Insulating Oil | | | | Kinematic Viscosity (cSt at 30° C.) | CSV (kV) | CEV (kV) | Breakdown Time (Relative Value) |
|---|---|---|---|---|---|---|---|---|
| | Insulating Oil of (a) | wt % | Olefin | wt % | | | | |
| | benzyl) ether | | (4'-vinylphenyl)-ethylene | | | | | |

What is claimed is:

1. An electrical insulating oil consisting essentially of:
   (a) at least one electrical insulating oil selected from the group consisting of organic acid esters, animal oils, vegetable oils and aromatic ethers, and
   (b) 0.01 to 50% by weight of at least one of aromatic monoolefins and/or aromatic diolefins each having two condensed or noncondensed aromatic nuclei.
2. The electrical insulating oil in claim 1, wherein the viscosity of said electrical insulating oil is not higher than 30 cSt ($3 \times 10^{-5}$ m²/s) at 40° C.
3. The electrical insulating oil in claim 1, wherein said aromatic monoolefins are represented by the following general formulae (I) to (IV):

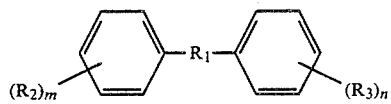
(I)

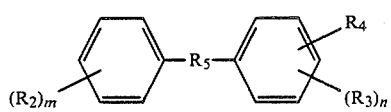
(II)

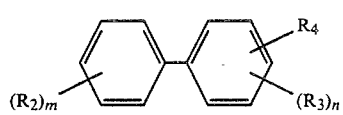
(III)

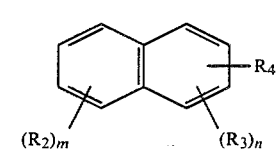
(IV)

wherein $R_1$ is an alkenylene or cycloalkenylene group, each of $R_2$ and $R_3$ is a hydrogen atom or an alkyl group, $R_4$ is an alkenyl or cycloalkenyl group, $R_5$ is an alkylene or cycloalkylene group, each of m and n is an integer from zero to three, inclusive, and $R_2$ of m in number and $R_3$ of n in number are the same groups or different groups from one another.

4. The electrical insulating oil in claim 1, wherein said aromatic diolefins are represented by the following general formulae (V) to (VII):

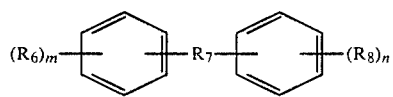
(V)

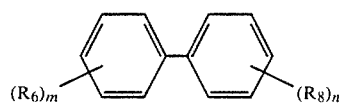
(VI)

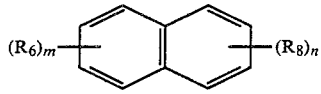
(VII)

wherein each of $R_6$, $R_7$ and $R_8$ is a hydrocarbon residual group, each of m and n is an integer from zero to three, inclusive, $R_6$ of m in number, $R_7$, and $R_8$ of n in number are the same groups or different groups from one another, and the total number of double bonds in said hydrocarbon residual groups is two.

5. An oil-filled electrical appliance which is impregnated with an electrical insulating oil consisting essentially of:
   (a) at least one electrical insulating oil selected from the group consisting of organic acid esters, animal oils, vegetable oils, and aromatic ethers, and
   (b) 0.01 to 50% by weight of at least one of aromatic monoolefins and/or aromatic diolefins each having two condensed or noncondensed aromatic nuclei.
6. The oil-filled electrical appliance in claim 5, wherein the viscosity of said electrical insulating oil is not higher than 30 cSt ($3 \times 10^{-5}$ m²/s) at 40° C.
7. The oil-filled electrical appliance in claim 5, wherein said aromatic monoolefins are represented by the following general formulae (I) to (IV):

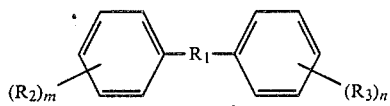
(I)

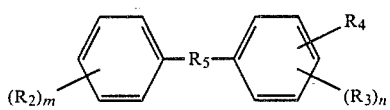
(II)

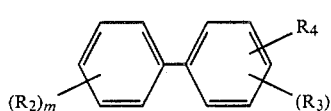
(III)

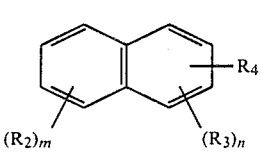
(IV)

wherein $R_1$ is an alkenylene or cycloalkenylene group, each of $R_2$ and $R_3$ is a hydrogen atom or an alkyl group, $R_4$ is an alkenyl or cycloalkenyl group, $R_5$ is an alkylene or cycloalkylene group, each of m and n is an integer from zero to three, inclusive, and $R_2$ of m in number and $R_3$ of n in number are the same groups or different groups from one another.

8. The oil-filled electrical appliance of claim 5, wherein said aromatic diolefins are represented by the following general formulae (V) to (VII):

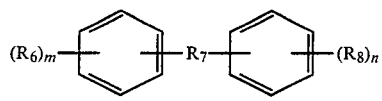
(V)

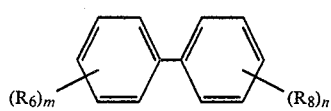
(VI)

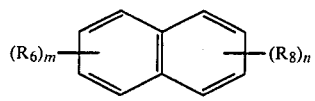
(VII)

wherein each of $R_6$, $R_7$ and $R_8$ is a hydrocarbon residual group, each of m and n is an integer from zero to three, inclusive, $R_6$ of m in number, $R_7$, and $R_8$ of n in number are the same groups or different groups from one another, and the total number of double bonds in said hydrocarbon residual groups is two.

9. The oil-filled electrical appliance in claim 5, wherein said electrical appliance is one member selected from the group consisting of oil-filled capacitors, oil-filled cables and transformers.

10. The oil-filled electrical appliance in claim 5, wherein the insulating material or dielectric material used in said oil-filled electrical appliance is insulating paper, synthetic resin film or their combination.

11. The oil-filled electrical appliance in claim 5, wherein said synthetic resin film is polyethylene film or polypropylene film.

* * * * *